(12) United States Patent
Panin (10) Patent No.: US 8,110,805 B2
(45) Date of Patent: Feb. 7, 2012

(54) ITERATIVE ALGORITHMS FOR CRYSTAL EFFICIENCIES ESTIMATIONS FROM TOF COMPRESSED NORMALIZATION DATA

(75) Inventor: Vladimir Y. Panin, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 473 days.

(21) Appl. No.: 12/463,903

(22) Filed: May 11, 2009

(65) Prior Publication Data

US 2010/0072375 A1 Mar. 25, 2010

Related U.S. Application Data

(60) Provisional application No. 61/127,037, filed on May 9, 2008.

(51) Int. Cl.
*G01T 1/164* (2006.01)

(52) U.S. Cl. .................................................. 250/362

(58) Field of Classification Search .................. 250/362, 250/363.03, 363.04, 363.09; 382/128; 700/85, 700/104
See application file for complete search history.

(56) References Cited

U.S. PATENT DOCUMENTS

| | | | |
|---|---|---|---|
| 6,858,847 B1 | 2/2005 | Macciocchi | |
| 2007/0036418 A1* | 2/2007 | Pan et al. | 382/131 |
| 2007/0176087 A1 | 8/2007 | Wang et al. | |
| 2008/0099686 A1* | 5/2008 | Defrise et al. | 250/363.04 |
| 2008/0180580 A1* | 7/2008 | Kadrmas | 348/744 |
| 2008/0217540 A1* | 9/2008 | Panin et al. | 250/363.03 |

* cited by examiner

*Primary Examiner* — David Porta
*Assistant Examiner* — Marcus Taningco
(74) *Attorney, Agent, or Firm* — Peter L. Kendall (57) ABSTRACT

Time-of-flight (TOF) clinical data collected during a PET scan are very sparse and have significant size. These data undergo TOF axial rebinning and azimuthal mashing if histogrammed data-based reconstruction algorithms are used. In a clinical environment, TOF compression is typically performed by the hardware rebinner. Normalization data, acquired on a regular basis and used for estimation of some norm components, are compressed by the hardware rebinner in a similar manner. This disclosure presents simple update iterative algorithms for crystal efficiencies norm component estimation from TOF compressed normalization data. Previously known methods are not directly applicable since the compression procedure significantly complicates normalization data model equations. The iterative algorithms presented herein have advantages of being easily adapted to any acquisition geometry, and of allowing estimation of parameters at crystal level when a number of crystals is relatively small. A monotonic sequential coordinate descent algorithm, which optimizes the Least Squares objective function, is presented. A simultaneous update algorithm, which possesses the advantage of easy parallelization, is also presented.

20 Claims, 5 Drawing Sheets

ITERATIVE ALGORITHMS FOR CRYSTAL EFFICIENCIES ESTIMATIONS FROM TOF COMPRESSED NORMALIZATION DATA

BACKGROUND OF THE INVENTION

1. Technical Field

In general, the present disclosure relates to nuclear medical imaging. More particularly, the disclosure relates to Positron Emission Tomography (PET) imaging and accurate estimation of scintillation crystal efficiency of PET detector blocks in a PET system.

2. General Background of the Invention

Nuclear medicine is a unique specialty wherein radiation emission is used to acquire images that show the function and physiology of organs, bones or tissues of the body. The technique of acquiring nuclear medicine images entails first introducing radiopharmaceuticals into the body—either by injection or ingestion. These radiopharmaceuticals are attracted to specific organs, bones, or tissues of interest. Upon arriving at their specified area of interest, the radiopharmaceuticals produce gamma photon emissions, which emanate from the body and are then captured by a scintillation crystal. The interaction of the gamma photons with the scintillation crystal produces flashes of light, which are referred to as "events." Events are detected by an array of photo detectors (such as photomultiplier tubes), and their spatial locations or positions are then calculated and stored. In this way, an image of the organ or tissue under study is created from detection of the distribution of the radioisotopes in the body.

One particular nuclear medicine imaging technique is known as positron emission tomography, or PET. PET is used to produce images for diagnosing the biochemistry or physiology of a specific organ, tumor or other metabolically active site. The measurement of tissue concentration using a positron emitting radionuclide is based on coincidence detection of the two gamma photons arising from a positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors; i.e., the gamma photon emissions are detected virtually simultaneously by each detector. When two oppositely disposed gamma photons each strike an oppositely disposed detector to produce a time coincidence event, they also identify a line-of-response (LOR) along which the annihilation event has occurred. An example of a PET method and apparatus is described in U.S. Pat. No. 6,858,847, which patent is incorporated herein by reference in its entirety.

Figure 1:
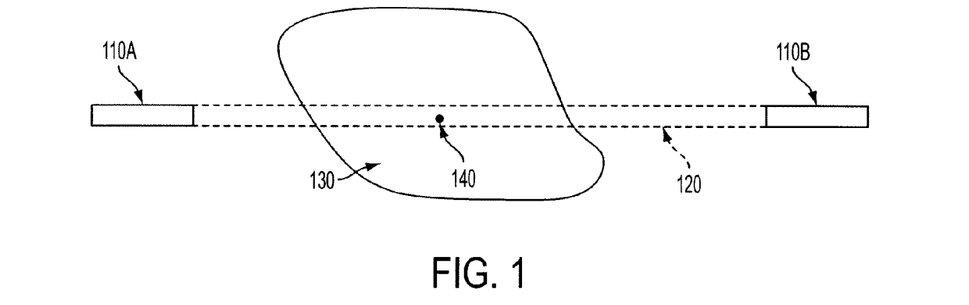
FIG. 1 shows a conceptual representation of a LOR in PET imaging.

FIG. 1 is a graphic representation of a line of response. An annihilation event 140 occurring in imaged object mass 130 may emit two simultaneous gamma rays (not shown) traveling substantially 180° apart. The gamma rays may travel out of scanned mass 130 and may be detected by block detectors 110A and 110B, where the detection area of the block detector defines the minimum area or maximum resolution within which the position of an incident gamma ray may be determined. Since block detectors 110A and 110B are unable to determine precisely where the gamma rays were detected within this finite area, the LOR 120 connecting block detectors 110A and 110B may actually be a tube with its radius equal to the radius of block detectors 110A and 110B. Similar spatial resolution constraints are applicable to other types of detectors, such as photomultiplier tubes.

To minimize data storage requirements, clinical projection data are axially compressed, or mashed, to within a predetermined span. With a cylindrical scanner, which has translational symmetry, the geometrical blurring resulting from axial compression may be modeled by projecting a blurred image into LOR space, followed by axial compression. This eliminates the storage of the axial components, and special algorithms have been developed to incorporate system response. The system response modeling then will allow the use of standard reconstruction algorithms such as Joseph's Method, and a reduction of data storage requirements.

The LOR defined by the coincidence events are used to reconstruct a three-dimensional distribution of the positron-emitting radionuclide within the patient. In two-dimensional PET, each 2D transverse section or "slice" of the radionuclide distribution is reconstructed independently of adjacent sections. In fully three-dimensional PET, the data are sorted into sets of LOR, where each set is parallel to a particular detector angle, and therefore represents a two dimensional parallel projection $p(s, \Phi)$ of the three dimensional radionuclide distribution within the patient, where "s" corresponds to the displacement of the imaging plane perpendicular to the scanner axis from the center of the gantry, and "$\Phi$" corresponds to the angle of the detector plane with respect to the x axis in (x, y) coordinate space (in other words, $\Phi$ corresponds to a particular LOR direction).

Figure 2:
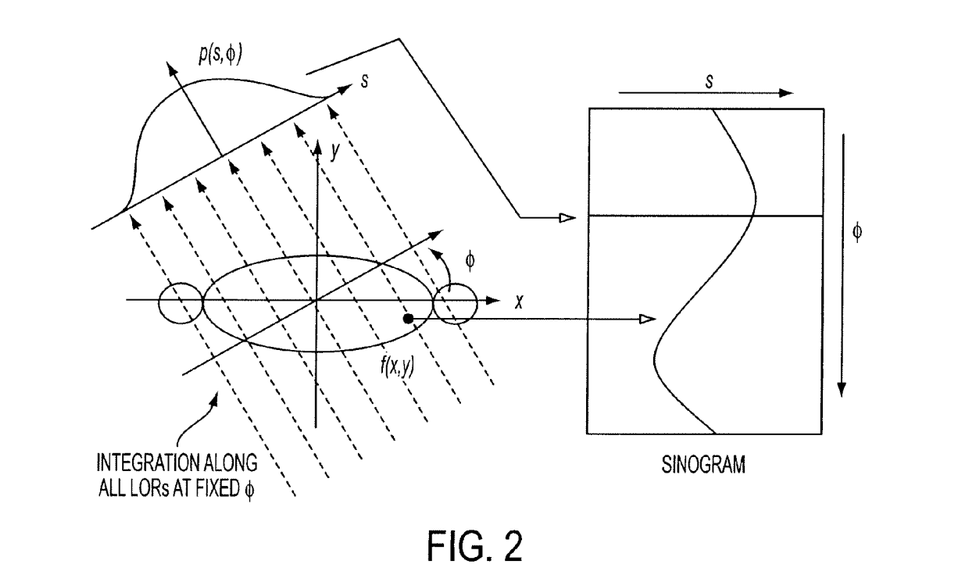
FIG. 2 is an illustration of the development of a sonogram.

Coincidence events are integrated or collected for each LOR and stored in a sinogram. In this format, a single fixed point in $f(x, y)$ traces a sinusoid in the sinogram. In each sinogram, there is one row containing the LOR for a particular azimuthal angle $\Phi$; each such row corresponds to a one-dimensional parallel projection of the tracer distribution at a different coordinate along the scanner axis. This is shown conceptually in FIG. 2.

It is known that the efficiency of the crystals in the detector modules or blocks of a PET scanner will vary from crystal to crystal in terms of luminescence per gamma strike. Therefore, it is important to estimate accurately the crystal efficiency of each detector in order to obtain good normalization for 3D PET data. Inaccurate knowledge of crystal efficiency can lead to artifacts, higher noise in the image, and/or poor uniformity in the reconstructed image.

Normalization factors are corrections that compensate for non-uniformity of the PET detector pair efficiencies. A component-based method is commonly used to improve accuracy of the normalization factors. Most components, such as geometrical and crystal interference components, can be estimated or computed in advance for a particular scanner type. The crystal efficiency component must be estimated relatively often for each physical scanner.

Recent developments in clinical PET systems allow the measurement of the time-of-flight (TOF) difference between the two coincident photons with a resolution as low as 500 ps full-width half-maximum (FWHM). This leads to improved signal-to-noise ratio when large patients are imaged. The TOF acquisition results in additional data dimensions that significantly increase data size. One practical approach is to use list mode reconstruction. However, such reconstruction depends on the number of registered events and therefore is time consuming for high count studies. This reconstruction is also possible with only certain algorithms. On the other hand, due to the redundancy of TOF information, data can be compressed without loss of resolution. Such compression may consist of axial rebinning and azimuthal mashing. These are useful if reconstruction algorithms from histogrammed data are exploited. Then reconstruction time is independent of acquisition time and any reconstruction algorithms are ready to be used.

In a clinical environment, normalization data are acquired with the same hardware TOF rebinner on a regular basis. TOF compression complicates basic equations behind the normalization data model and special methods should be developed to estimate normalization components.

A number of methods to estimate crystal efficiencies from uncompressed LOR or list mode normalization data have been developed. For example, the method from Defrise is an analytical method that typically uses only part of the available data. The fan sum method, which tries to use all available data, is not exact and might lead to bias in a very uneven efficiency distribution. Analytical methods allow for fast processing of data. However, this method might not be required in the clinical environment, where the normalization scan is performed separately and there is enough time to process it.

On the other hand, crystal efficiencies can be estimated by the Maximum Likelihood (ML) approach. The iterative approach has the advantage of versatility, where all available data are easily accommodated. It is truly a statistical method. Moreover, normalization scan object position can be more or less arbitrary. This approach results in solving a large system of nonlinear equations iteratively, and is consequently potentially resource consuming.

TOF compression complicates basic equations behind the normalization data model. Therefore, the mentioned methodologies are not directly applicable. Accordingly, there is a need in the art for a method for estimating crystal efficiency components from TOF compressed normalization data.

SUMMARY OF THE INVENTION

An object of embodiments of the present disclosure is to provide simple update iterative algorithms for crystal efficiencies norm component estimation from TOF compressed normalization data. Previously known methods of norm component estimation are not directly applicable since compression procedures significantly complicate normalization data model equations. The methods presented herein have the advantages of easy adaptation to any acquisition geometry, and of allowing estimation of parameters at the crystal level when the number of crystals is relatively small. A monotonic sequential coordinate descent algorithm, which optimizes the Least Squares objective function, is disclosed. A simultaneous update algorithm, which possesses the advantage of easy parallelization, is also disclosed.

DETAILED DESCRIPTION OF THE INVENTION

TOF Data Compression

During a PET scan, a cylinder sinogram M generated based on data collected during the scan, the cylinder sinogram is parameterized by $\rho, \theta, \zeta, t$, where $\rho$ is the radial index, $\theta$ is the azimuthal index, $\zeta$ is the axial plane index (including oblique and direct planes), and t is the TOF bin index. The mashing/rebinning equation of the LOR connecting two crystals i and j is assumed to be known. In one example, the modeled measured sinogram is presented as $$\overline{M}_{\rho,\theta,\zeta,t} = \frac{1}{2}\sum_{i,j} \omega_{\rho\theta\zeta t,ij} T_{t,ij} \varepsilon_i \varepsilon_j \qquad (1)$$

where $\varepsilon$ is the crystal efficiency and T is the TOF cylinder projection in LOR space, with application of norm factors of already known components, attenuation, etc. The $\omega$ is the LOR contribution factor:

$$\omega_{\rho\theta\zeta t,ij} = \begin{cases} 1, & \text{if } ij \text{ contribute to sinogram bin}(\rho, \theta, \zeta, t) \\ 0, & \text{otherwise.} \end{cases} \qquad (2)$$

The factor is ½ is due to double summation over crystal indices.

A compression method, for example mashing or rebinning, may be used to preserve natural LOR sampling. During TOF compression, existing LOR values may be assigned to a set of virtual LORs. A cylindrical scanner has non-equidistant sampling in the radial direction. Polar angle sampling depends on radial coordinates. TOF mashing and rebinning can preserve such natural sampling characteristics by appropriate choice of virtual LORs. Then TOF bin zero will represent a regularly axially spanned sinogram mashed in the azimuthal direction, assuming a relatively small mashing factor. This results in a relatively smooth sinogram, at least for t=0. In one embodiment, it can be assumed that list mode provided a 312 ps TOF bin, since this bin size is used in reconstruction. For such a wide time bin, the TOF index does not change in assignment to virtual LOR.

Figure 3:
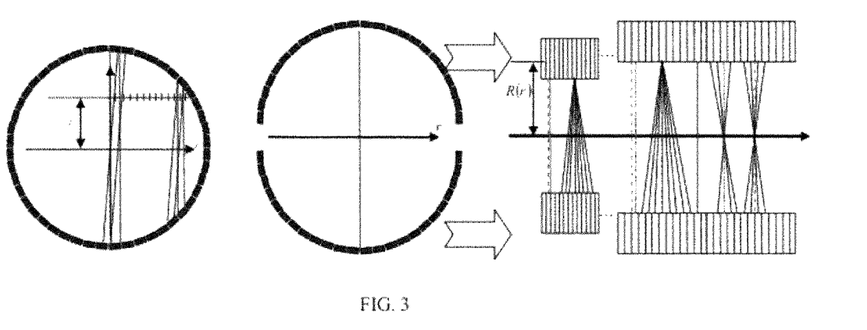
FIG. 3 is an illustration with an azimuthal mashing.

At zero TOF bin, all LORs approximately intersect virtual ones; see FIG. 3. Virtual LORs represent non-equidistant radial sampling. Existing LOR azimuthal angles are defined by crystal pairs; this is independent of the TOF bin. Then a radial shift between virtual LORs with regards to t=0 is considered in the assignment of existing LORs, when t is not zero. In this example, a mash factor 4 is used.

To simplify the rebinning process, one can assume that it is independent of radial mashing. Virtual LORs are chosen similarly to the case of regular span non-TOF compression. All existing LORs have the same axial coordinate at t=0, since this is a property of cylindrical scanners; see FIG. 4. Therefore, all LORs intersect at one point of the axial axis. Then axial shift with regards to t=0 is considered as a function of the TOF bin value to choose the closest virtual LOR in the axial direction.

In summary, the mashing/rebinning scheme preserved cylindrical scanner natural LOR sampling. This exemplary embodiment is implemented as 1D interpolation in the radial direction and 1D interpolation in the axial direction in the assignment of existing LORs to virtual ones, depending on the TOF bin.

Objective Function

Equation (1) assumes summation of Poisson variables. Nevertheless, in one embodiment, we would like to minimize the following Least Squares (LS) (Gaussian model) objective function:

$$L = \sum_{\rho,\theta,\zeta,t} \frac{(M_{\rho\theta\zeta t} - \overline{M}_{\rho\theta\zeta t})^2}{\sigma^2_{\rho\theta\zeta t}} \quad (3)$$

This objective function does not properly reflect the statistical nature of data, but it facilitates the development of the following algorithms. Moreover, in order to use the Poisson Likelihood function, one can consider the scattering and randoms events in (1). However, in this embodiment, we will ignore scatter and perform a randoms subtraction in $M_{\rho\theta\zeta t}$, so that its value can be negative. In addition to this, a normalization scan is typically a high count scan, justifying the use of the LS objective function.

In the following, for simplicity, we will omit $\sigma_{\rho\theta\zeta t}$ in the derivation. Its inclusion is straightforward by scaling of measured and modeled data.

FIG. 3 is an illustration with an azimuthal mashing with factor 4. For a particular azimuthal angle, the PET scanner may be considered to be separated into two half circles. Each half circle presents virtual local detector with non-equidistant sampling and varying distance between virtual detectors. Eight LORs with detector difference [−4, 3] are assumed to have the same azimuthal angles. Such LORs construct two complexes, represented by vertical virtual LORs. The vertical virtual LOR coincides with the existing one. The dashed LOR is purely virtual. Assignment of existing LOR to virtual depends on TOF coordinate t and may be implemented as radial shift with regards to t=0.

Figure 4:
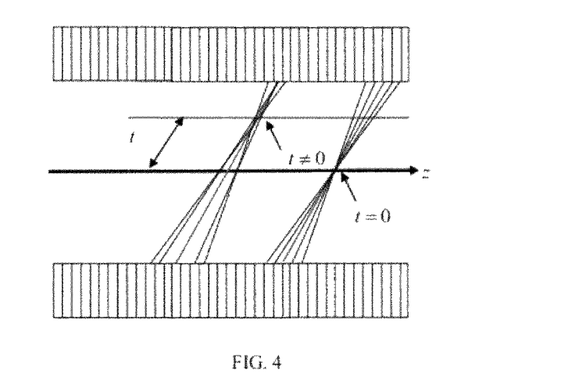
FIG. 4 illustrates axial TOF rebinning with span 11.
Figure 5:
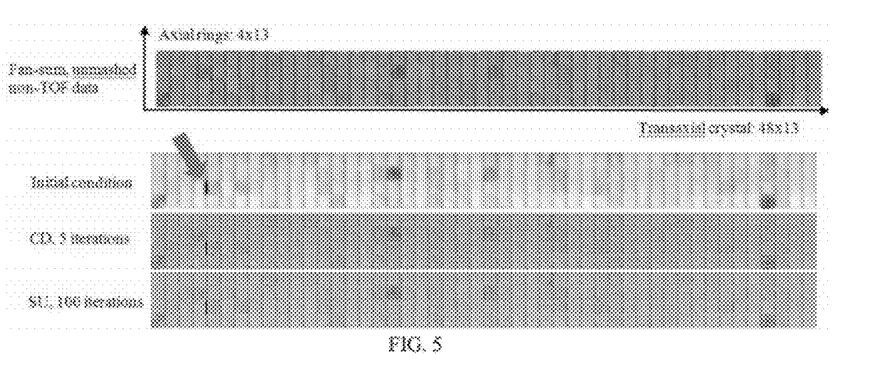
FIG. 5 illustrates crystal efficiencies estimation with a bad scanner setup and a 30-minute acquisition, wherein an arrow shows strip of non-functioning crystals.

FIG. 4 illustrates axial TOF rebinning with span 11. Virtual LORs represent span complexes, which are the same as in non-TOF cases. Assignment of existing LORs to virtuals depends on TOF coordinate t and, in one embodiment, is implemented as LOR axial shift with regards to t=0.

Coordinate Descent (CD) Algorithm

In one embodiment, we derive a simple update equation of the CD method where the objective function is minimized with respect to one parameter, while the rest are fixed.

If one minimizes (3) only with respect to one parameter, say $\epsilon_k$, then this equation may be solved:

$$0 = \frac{\partial}{\partial \epsilon_k} L = \sum_{\rho,\theta,\zeta,t} \left( M_{\rho\theta\zeta t} - \frac{1}{2} \sum_{i,j} \omega_{\rho\theta\zeta t,ij} T_{t,ij} \epsilon_i \epsilon_j \right) \times \quad (4)$$

$$\left( -\sum_{i,j} \omega_{\rho\theta\zeta t,ij} T_{t,ij} (\delta_{i,k} \epsilon_j + \epsilon_i \delta_{j,k}) \right).$$

The equation can be solved for $\epsilon_k$, taking into account that $\omega_{\rho\theta\zeta t,ij}=0$ if i=j, since the crystal is never in coincidence with itself. Therefore, the second multiplication factor in (4) does not contain $\epsilon_k$. Then the equation is linear with regards to $\epsilon_k$. This can be written explicitly, extracting $\epsilon_k$ from the first multiplicative factor in (6):

$$\sum_{\rho,\theta,\zeta,t} \left( M_{\rho\theta\zeta t} - \frac{1}{2} \sum_{i \neq k, j \neq k} \omega_{\rho\theta\zeta t,ij} T_{t,ij} \epsilon_i \epsilon_j \right) \left( \sum_{j \neq k} \omega_{\rho\theta\zeta t,kj} T_{t,kj} \epsilon_j \right) - \quad (5)$$

$$\epsilon_k \sum_{\rho,\theta,\zeta,t} \left( \sum_{i \neq k} \omega_{\rho\theta\zeta t,ki} T_{t,ki} \epsilon_i \right) \left( \sum_{j \neq k} \omega_{\rho\theta\zeta t,kj} T_{t,kj} \epsilon_j \right) = 0.$$

It can be rewritten in additive iterative form to update variable $\epsilon_k$ with respect to the previous value. The expression will have term $\overline{M}_{\rho\theta\zeta t}$, estimated using the previous value of $\epsilon_k$:

$$\epsilon_k^{(new)} = \epsilon_k^{(old)} + \frac{\sum_{\rho,\theta,\zeta,t} (M_{\rho\theta\zeta t} - \overline{M}_{\rho\theta\zeta t}(\epsilon^{(m)})) \left( \sum_{j \neq k} \omega_{\rho\theta\zeta t,kj} T_{t,kj} \epsilon_j \right)}{\sum_{\rho,\theta,\zeta,t} \left( \sum_{j \neq k} \omega_{\rho\theta\zeta t,kj} T_{t,kj} \epsilon_j \right)^2}. \quad (6)$$

One convenient implementation is crystal-driven. For each crystal k, one may consider all corresponding opposite crystals in the cylinder shadow. From the knowledge of two particular crystals, the corresponding sinogram bin is accessed. A crystal-driven equation can be illustrated as:

$$\epsilon_k^{(n)} = \epsilon_k^{(n-1)} + \frac{\sum_{j \neq k} \epsilon_j^{(n,k)} \sum_t T_{t,kj} \omega_{\rho\theta\zeta t,kj} (M_{\rho\theta\zeta t} - \overline{M}_{\rho\theta\zeta t}(\epsilon_k^{(n,k)}))}{\sum_{j \neq k} \epsilon_j^{(n,k)} \sum_{j' \neq k} \epsilon_{j'}^{(n,k)} \sum_t T_{t,kj} T_{t,kj'} \sum_{\rho,\theta,\zeta} \omega_{\rho\theta\zeta t,kj} \omega_{\rho\theta\zeta t,kj'}} \quad (7)$$

$$\epsilon^{(n,k)} = \{\epsilon_0^{(n)}, \epsilon_1^{(n)}, \ldots, \epsilon_{k-1}^{(n)}, \epsilon_k^{(n-1)}, \epsilon_{k+1}^{(n-1)}, \ldots\}. \quad (8)$$

Here, n is the iteration number. A single iteration may consist of updating of all crystal efficiency values. The summation over sinogram indices was explicitly removed in the numerator: $\rho\theta\zeta$ is uniquely defined by the k-j pair and t. Definition (8) represents the basic idea of a sequential CD algorithm: the very last update of crystal efficiencies may be used in estimation of the current crystal efficiency. This definition implies that the update is performed according to the crystal index. The crystal with index zero is updated first, then the crystal with index 1, and so on.

The CD algorithm is difficult to parallelize. In this embodiment, the value $\overline{M}_{\rho\theta\zeta t}$ depends on the cluster of crystals of the same blocks due to mashing and rebinning Therefore, this term should be updated immediately after the update of every crystal efficiency. When the k crystal is updated, a loop over the corresponding opposite crystals in coincidence is performed, subtracting the old value of the product of the k crystal and the crystal in coincidence efficiencies, and adding a multiplicative term with the new crystal efficiency in corresponding $\overline{M}_{\rho\theta\zeta t}$. This update is prone to a round off error when many iterations are performed. To exclude this effect, $\overline{M}_{\rho\theta\zeta t}$ was recomputed at every iteration when the value of the objective function was estimated.

In this embodiment, the computing of the denominator in the CD algorithm is cumbersome too, since it contains a double loop. The mashing/rebinning scheme binds together closely spaced crystals. Therefore, the loop over the j index is performed in the same manner as in the numerator. In the loop over j' consider only the closely spaced crystal to j by exploiting a mask in the transaxial and axial directions.

Simultaneous Update (SU) Algorithm

In another embodiment, algorithms of gradient type are derived. In this embodiment, the LS objective function algorithm has a simple update equation at iteration n:

$$\varepsilon_k^{(n)} = \varepsilon_k^{(n-1)} - \alpha_k^{(n-1)} \frac{\partial L(\varepsilon^{(n-1)})}{\partial \varepsilon_k} \quad (9)$$

surrogate function may be used to derive a positive value step size $\alpha$. It is assumed that an objective function can be well approximated by second order Taylor's expression with regards to a current efficiencies estimate of iteration n-1:

$$L(\varepsilon) \approx T_1(\varepsilon, \varepsilon^{(n-1)}) = L(\varepsilon^{(n-1)}) + \sum_l \frac{\partial L(\varepsilon^{(n-1)})}{\partial \varepsilon_l}(\varepsilon_l - \varepsilon_l^{(n-1)}) + \frac{1}{2} \sum_{l,m} \frac{\partial^2 L(\varepsilon^{(n-1)})}{\partial \varepsilon_l \partial \varepsilon_m}(\varepsilon_l - \varepsilon_l^{(n-1)})(\varepsilon_m - \varepsilon_m^{(n-1)}). \quad (10)$$

$\Delta\varepsilon_l$ may be defined as $\Delta\varepsilon_l = (\varepsilon_l - \varepsilon_l^{(n-1)})$. Using non equalities $$\Delta\varepsilon_l \Delta\varepsilon_m \leq \frac{1}{2}(\Delta\varepsilon_l^2 + \Delta\varepsilon_m^2) - \Delta\varepsilon_l \Delta\varepsilon_m \leq \frac{1}{2}(\Delta\varepsilon_l^2 + \Delta\varepsilon_m^2) \quad (11)$$

a separable surrogate function can be constructed:

$$T_1(\varepsilon, \varepsilon^{(n-1)}) \leq T_2(\varepsilon, \varepsilon^{(n-1)}) = \quad (12)$$

$$L(\varepsilon^{(n-1)}) + \sum_l \frac{\partial L(\varepsilon^{(n-1)})}{\partial \varepsilon_l}(\varepsilon_l - \varepsilon_l^{(n-1)}) + \frac{1}{2} \sum_{l,m} \left| \frac{\partial^2 L(\varepsilon^{(n-1)})}{\partial \varepsilon_l \partial \varepsilon_m} \right| \frac{(\varepsilon_l - \varepsilon_l^{(n-1)})^2 + (\varepsilon_m - \varepsilon_m^{(n-1)})^2}{2}.$$

Here, the absolute value of $$\frac{\partial^2 L}{\partial \varepsilon_l \partial \varepsilon_m}$$

is used. The value and the gradient of the surrogate function $T_2(\varepsilon, \varepsilon^{(n-1)})$ coincides with the ones of the $T_1(\varepsilon, \varepsilon^{(n-1)})$ objective function at $\varepsilon^{(n-1)}$. The surrogate function lies above $T_1(\varepsilon, \varepsilon^{(n-1)})$. In approximation $$M_{\rho\theta\zeta t} \approx \overline{M}_{\rho\theta\zeta t} \quad (13)$$

which is accurate close to the solution, $\partial^2 L/\partial\varepsilon_l\partial\varepsilon_m$ is positive, assuming positive $\varepsilon^{(n-1)}$, so the surrogate function closely approximates that of the truncated series. However, the positivity of $\partial^2 L/\partial\varepsilon_l\partial\varepsilon_m$ is not necessary in general, and the second of the nonequalities of (11) is used to construct the surrogate function if this term is negative. If expansion (10) is sufficiently accurate, the algorithm of this embodiment will show monotonic behavior; however, this property is not guaranteed by the present embodiment.

Finally, the update equation for the LS objective function, using approximation (13) in term $\partial^2 L/\partial\varepsilon_l\partial\varepsilon_m$, which only defines step size, has the form:

$$\varepsilon_k^{(n)} = \varepsilon_k^{(n-1)} + \frac{\sum_{j \neq k} \varepsilon_j^{(n-1)} \sum_t \omega_{\rho\theta\zeta t,kj} T_{t,kj}(M_{\rho\theta\zeta t} - \overline{M}_{\rho\theta\zeta t}(\varepsilon^{(n-1)}))}{\sum_{j \neq k} \varepsilon_j^{(n-1)} \sum_t \omega_{\rho\theta\zeta t,kj} T_{t,kj} E_{\rho\theta\zeta t}^{(n-1)}} \quad (14)$$

where $$E_{\rho\theta\zeta t}^{(n-1)} = \frac{1}{2} \sum_{ij} \omega_{\rho\theta\zeta t,ij} T_{t,ij}(\varepsilon_i^{(n-1)} + \varepsilon_j^{(n-1)}). \quad (15)$$

Once again summation over sinogram indices was explicitly removed in (14)-(15): $\rho\theta\zeta$ is uniquely defined by the k-j pair and t.

The main advantage of algorithm is that it is straightforwardly easy to parallelize. Non-negativity constraint is implemented in the same way as in the case of CD algorithms. If the efficiency update has a negative value, it can be replaced by some small positive value.

Initial Condition

The CD algorithm is sensitive to the initial condition. The use of a truncated expansion in the SU algorithm derivation is justified close to the solution. The solution also allows for a negative value of crystal efficiency. It is possible to find a good initial condition. An initial condition that provides a positive value of efficiencies is obtained through the global surrogate function of the LS objective function. This global surrogate function is separable in variables and it is trivial to find its stationary points.

The objective function (3) can be rewritten as $$L_1 = \sum_{\rho,\theta,\zeta,t} \left( -2M_{\rho\theta\zeta t} \frac{1}{2} \sum_{i,j} \omega_{\rho\theta\zeta t,ij} T_{t,ij} \varepsilon_i \varepsilon_j + \frac{1}{4} \sum_{i,j} \sum_{k,l} \omega_{\rho\theta\zeta t,ij} T_{t,ij} \omega_{\rho\theta\zeta t,kl} T_{t,kl} \varepsilon_i \varepsilon_j \varepsilon_k \varepsilon_l \right) + const. \quad (16)$$

In one embodiment, the following non-equality may be used to create a surrogate function that lies above the original one, replacing the second term of (16):

$$\varepsilon_i \varepsilon_j \varepsilon_k \varepsilon_l \leq \frac{1}{4}(\varepsilon_i^2 + \varepsilon_j^2 + \varepsilon_k^2 + \varepsilon_l^2). \quad (17)$$

Additionally, the following non-equality may be used in the creation of a separable surrogate function that lies below or above the original one, depending on the sign of $M_{\rho\theta\zeta t}$. Since $M_{\rho\theta\zeta t}$ should be positive most of the time, the surrogate function can be constructed to lie below the original one. In this embodiment, the first term of (16) can use this non-equality $$-\frac{1}{2}(\varepsilon_i^2 + \varepsilon_j^2) \leq \varepsilon_i \varepsilon_j \leq \frac{1}{2}(\varepsilon_i^2 + \varepsilon_j^2). \quad (18)$$

In this embodiment, the surrogate function coincides with the original objective function at zero efficiency and lies above the original objective function at large efficiency values:

$$L_2 = \sum_{\rho,\theta,\zeta,t} \left( -2|M_{\rho\theta\zeta t}| \frac{1}{2} \sum_{i,j} \omega_{\rho\theta\zeta t,ij} T_{t,ij} \varepsilon_i^2 + \right.$$

$$\left. \frac{1}{2} \sum_{i,j} \omega_{\rho\theta\zeta t,ij} T_{t,ij} \left( \frac{1}{2} \sum_{k,l} \omega_{\rho\theta\zeta t,kl} T_{t,kl} \right) \varepsilon_i^4 \right) + const. \quad (19)$$

The local maxima of this function correspond to a zero set, as expected. The local minima provides positive values of efficiencies:

$$\varepsilon_k^{(0)} = \sqrt{\frac{\frac{1}{2} \sum_{j \neq k} \sum_t \omega_{\rho\theta\zeta t,kj} T_{t,kj} |M_{\rho\theta\zeta t}|}{\frac{1}{2} \sum_{j \neq k} \sum_t \omega_{\rho\theta\zeta t,kj} T_{t,kj} \frac{1}{2} \sum_{lm} \omega_{\rho\theta\zeta t,lm} T_{t,lm}}}. \quad (20)$$

This serves as the initial condition to both algorithms.

The initial condition can be derived from the log of the Poisson Likelihood objective function; assuming non-negative $M_{\rho\theta\zeta t}$. We found that both initial conditions bring the solution closely to the minimum of the objective function. We use the surrogate function for the LS objective function to be consistent with the original LS optimization.

Figure 6:
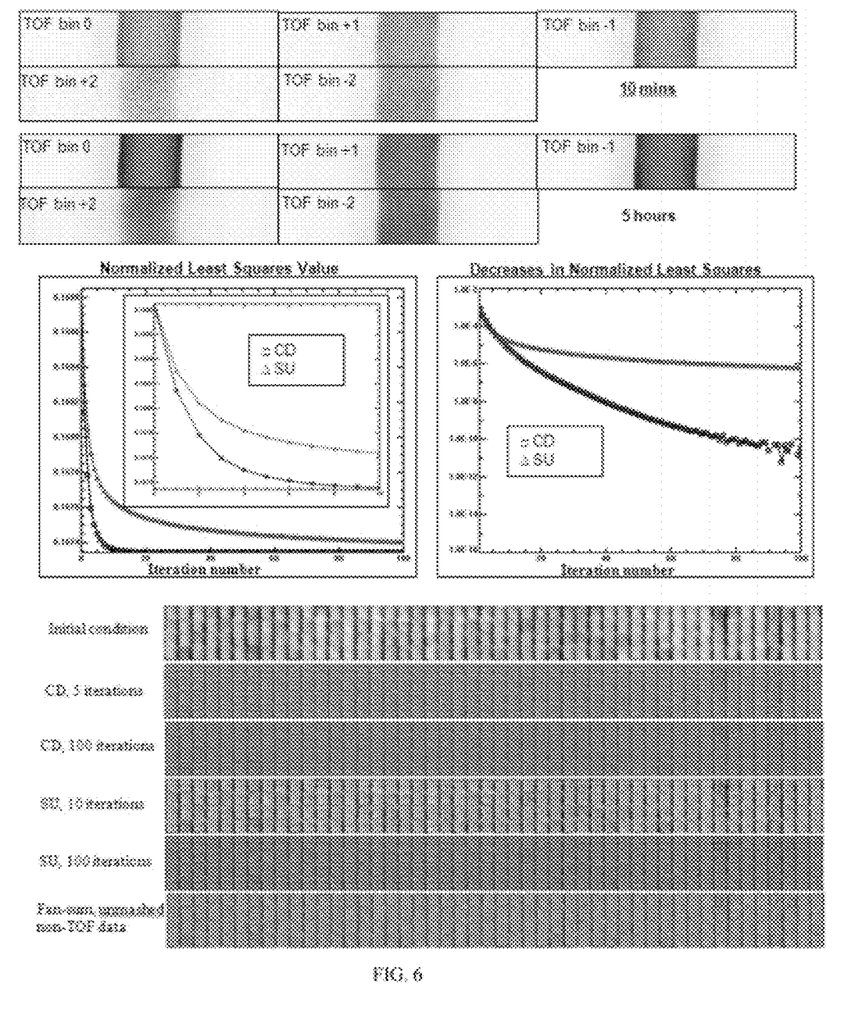
FIG. 6 illustrates crystal efficiencies estimation with a 10-minute acquisition.

FIG. 6 shows the performance of the exemplary embodiments in a 10 minute scan. Only the lowest index 5 TOF bins were used. These bins cover the cylinder object quite well, assuming TOF FWHW 550 ps and bin size 312 ps. Note that TOF bins in FIG. 6 are not perfectly centralized and have slight shift in t coordinate. The sinogram with the TOF index −1, +/−2 has high frequencies due to nearest neighbor interpolation. Note that TOF bin zero is not perfectly centralized and has slight shift in t coordinate. However, such high frequencies did not produce artifacts either in the crystal efficiencies distribution or in the image reconstruction. Both exemplary embodiments showed monotonical behavior. The SU updates provided a smoother singles distribution when compared to the CD method, when the same number of iterations was exploited. The CD algorithm converged to a smaller value of the normalized LS objective function quite fast.

Figure 7:
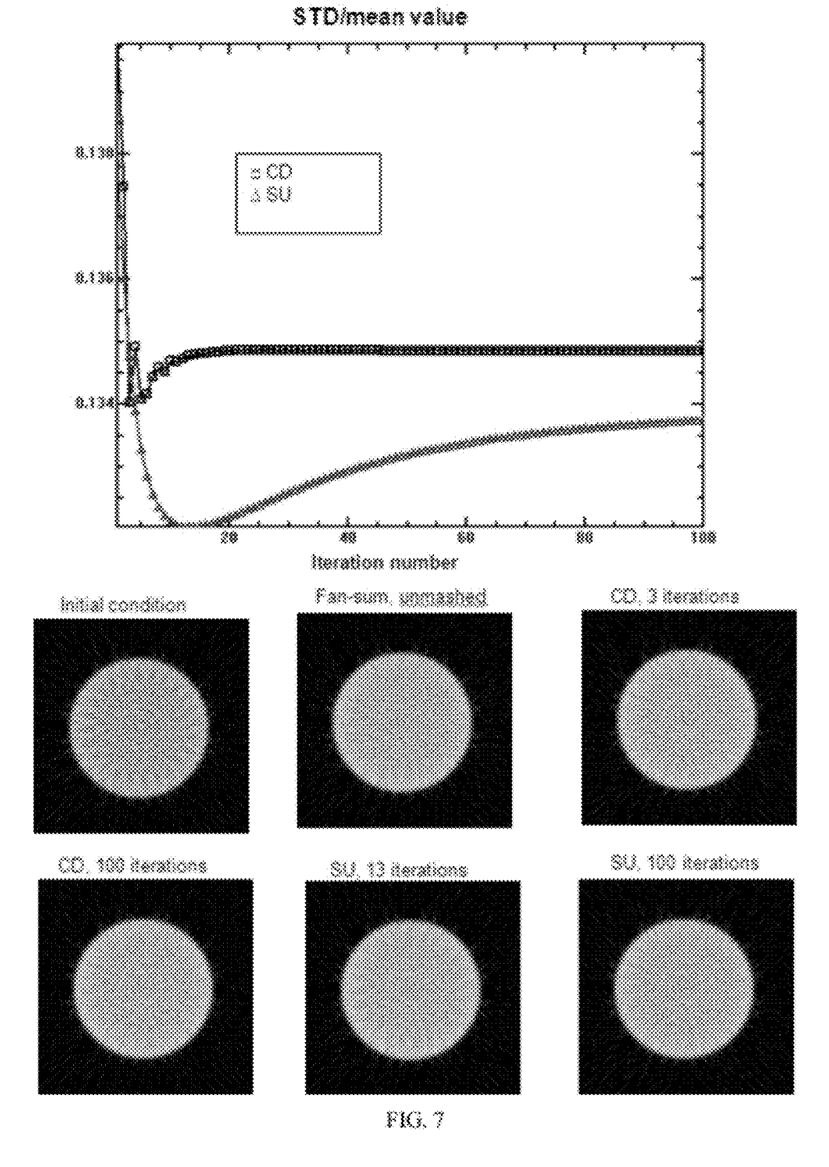
FIG. 7 illustrates optimization with respect to algorithm and number of iterations with data from a 5-hour acquisition used in FORE+FBP reconstruction.

Eventually, one needs to choose between algorithms and defining the number of iterations for a practical case. FIG. 7 represents the effort to access scanned cylinder uniformity as a function of iteration number. Five hours of data were corrected for attenuation, scatter, and normalization with a given iteration efficiency component. Then the data were rebinned by a FORE algorithm. It should be noted that the FORE application leads to loss of resolution and artifacts when there are a small number of azimuthal angles. However, for long uniform objects, this was not an issue. At the end, FBP reconstruction was performed. According to the uniform cylinder normalized standard deviation figure of merit, the exemplary embodiments should stop at a relatively small number of iterations: 3 for CD, and 13 min for SU methods. The SU norm provided a more uniform cylinder. As can be seen, application of norm, corresponding to the initial condition, led to visible artifacts in the image: rings, corresponding to the block structure, and doily artifacts. When the iteration proceeds, these artifacts start disappearing. At high iteration number noise in efficiency estimation will increase non-uniformity of the reconstructed image. Note that some faint ring artifacts are still present in the image. They are due to imperfections in the geometrical crystal interference norm component.

The singles estimation time was checked on a Xeon 3.4 GHz 64 bits CPU. Each iteration of the CD algorithm took about 15 minutes, while the SU method iteration took slightly less than 3 minutes. This included computation of LS values. Optimization of data storage, and flow and algorithm parallelization were not performed.

The exemplary iterative algorithms estimate the crystal efficiency normalization component. The CD algorithm converges extremely fast and can offset difficulties in its implementation. The SU algorithm leads to a slightly better image appearance, likely due to its intrinsic regularization property. This algorithm has an advantage of more easy implementation.

On a clinical scanner, the crystal efficiency component estimation might have an allowable processing time on the order of minutes. Therefore, these significantly better model iterative methods can eventually replace fast but sometimes very approximate analytical methods, such as fan-sum.

Those of ordinary skill may vary the data collection apparatus and methods for recording and processing the images without varying from the scope of the invention as defined in the appended claims.

What is claimed is:

1. A method of estimating crystal efficiency normalization components comprising:
    obtaining coincidence and TOF normalization data during a PET scan using a PET scanner;
    generating a measured cylinder sinogram and storing the measured cylinder sinogram in a computing device;
    compressing the TOF information, thereby generating compressed TOF normalization data; and
    performing a simple update iterative algorithm on the compressed TOF normalization data and cylinder sinogram measurements to generate an estimate of the crystal efficiency normalization components.

2. The method according to claim 1 further comprising modeling the cylinder sinogram.

3. The method according to claim 2, wherein the compression algorithm is selected from a group consisting of axial rebinning, azimuthal mashing, and axial rebinning and azimuthal mashing.

4. The method according to claim 3, wherein the simple update iterative algorithm is derived from a Least Squares objective function.

5. The method according to claim 4, wherein the cylinder sinogram is modeled using an equation $$\overline{M}_{\rho,\theta,\zeta,t} = \frac{1}{2} \sum_{i,j} \omega_{\rho\theta\zeta t,ij} T_{t,ij} \varepsilon_i \varepsilon_j,$$

wherein, $\rho$ is a radial index, $\theta$ is an azimuthal index, $\zeta$ is an axial plane index, t is a TOF bin index, $\epsilon$ represents crystal efficiency, T is a TOF cylinder projection in LOR space, and $\omega$ is a LOR contribution factor.

6. The method according to claim 5, wherein the Least Squares objective function comprises an equation $$L = \sum_{\rho,\theta,\zeta,t} \frac{(M_{\rho\theta\zeta t} - \overline{M}_{\rho\theta\zeta t})^2}{\sigma_{\rho\theta\zeta t}^2},$$

wherein M represents the cylinder sinogram measurements.

7. The method according to claim 6, wherein the simple update iterative algorithm comprises an equation $$\varepsilon_k^{(n)} = \varepsilon_k^{(n-1)} + \frac{\sum_{j \neq k} \varepsilon_j^{(n,k)} \sum_t T_{t,kj} \omega_{\rho\theta\zeta t,kj} (M_{\rho\theta\zeta t} - \overline{M}_{\rho\theta\zeta t}(\varepsilon_k^{(n,k)}))}{\sum_{j \neq k} \varepsilon_j^{(n,k)} \sum_{j' \neq k} \varepsilon_{j'}^{(n,k)} \sum_t T_{t,kj} T_{t,kj'} \sum_{\rho,\theta,\zeta} \omega_{\rho\theta\zeta t,kj} \omega_{\rho\theta\zeta t,kj'}},$$

wherein $$\varepsilon^{(n,k)} = \{\varepsilon_0^{(n)}, \varepsilon_1^{(n)}, \ldots, \varepsilon_{k-1}^{(n)}, \varepsilon_k^{(n-1)}, \varepsilon_{k+1}^{(n-1)}, \ldots\},$$

and n is an iteration number.

8. The method according to claim 6, wherein the simple update iterative algorithm comprises an equation $$\varepsilon_k^{(n)} = \varepsilon_k^{(n-1)} + \frac{\sum_{j \neq k} \varepsilon_j^{(n-1)} \sum_t \omega_{\rho\theta\zeta t,kj} T_{t,kj} (M_{\rho\theta\zeta t} - \overline{M}_{\rho\theta\zeta t}(\varepsilon^{(n-1)}))}{\sum_{j \neq k} \varepsilon_j^{(n-1)} \sum_t \omega_{\rho\theta\zeta t,kj} T_{t,kj} E_{\rho\theta\zeta t}^{(n-1)}},$$

wherein $$E_{\rho\theta\zeta t}^{(n-1)} = \frac{1}{2} \sum_{ij} \omega_{\rho\theta\zeta t,ij} T_{t,ij} (\varepsilon_i^{(n-1)} + \varepsilon_j^{(n-1)}),$$

and n is an iteration number.

9. The method according to claim 7 wherein an initial condition of the simple update iterative algorithm comprises a value represented by an equation $$\varepsilon_k^{(0)} = \sqrt{\frac{\frac{1}{2} \sum_{j \neq k} \sum_t \omega_{\rho\theta\zeta t,kj} T_{t,kj} |M_{\rho\theta\zeta t}|}{\frac{1}{2} \sum_{j \neq k} \sum_t \omega_{\rho\theta\zeta t,kj} T_{t,kj} \frac{1}{2} \sum_{lm} \omega_{\rho\theta\zeta t,lm} T_{t,lm}}}.$$

10. The method according to claim 8 wherein an initial condition of the simple update iterative algorithm comprises a value represented by an equation $$\varepsilon_k^{(0)} = \sqrt{\frac{\frac{1}{2} \sum_{j \neq k} \sum_t \omega_{\rho\theta\zeta t,kj} T_{t,kj} |M_{\rho\theta\zeta t}|}{\frac{1}{2} \sum_{j \neq k} \sum_t \omega_{\rho\theta\zeta t,kj} T_{t,kj} \frac{1}{2} \sum_{lm} \omega_{\rho\theta\zeta t,lm} T_{t,lm}}}.$$

11. A computer program embodied as computer-executable instructions stored on a non-transitory computer-readable medium for estimating crystal efficiency normalization components, the program comprising instructions for:
obtaining coincidence and TOF normalization data during a PET scan using a PET scanner;
generating a measured cylinder sinogram and storing the measured cylinder sinogram in a computing device;
compressing the TOF information, thereby generating compressed TOF normalization data; and
performing a simple update iterative algorithm on the compressed TOF normalization data and cylinder sinogram measurements to generate an estimate of the crystal efficiency normalization components.

12. The program according to claim 11 further comprising modeling the cylinder sinogram.

13. The program according to claim 12, wherein the compression algorithm is selected from a group consisting of axial rebinning, azimuthal mashing, and axial rebinning and azimuthal mashing.

14. The program according to claim 13, wherein the simple update iterative algorithm is derived from a Least Squares objective function.

15. The program according to claim 14, wherein the cylinder sinogram is modeled using an equation $$\overline{M}_{\rho,\theta,\zeta,t} = \frac{1}{2} \sum_{i,j} \omega_{\rho\theta\zeta t,ij} T_{t,ij} \varepsilon_i \varepsilon_j,$$

wherein, $\rho$ is a radial index, $\theta$ is an azimuthal index, $\zeta$ is an axial plane index, t is a TOF bin index, $\epsilon$ represents crystal efficiency, T is a TOF cylinder projection in LOR space, and $\omega$ is a LOR contribution factor.

16. The program according to claim 15, wherein the Least Squares objective function comprises an equation $$L = \sum_{\rho,\theta,\zeta,t} \frac{(M_{\rho\theta\zeta t} - \overline{M}_{\rho\theta\zeta t})^2}{\sigma_{\rho\theta\zeta t}^2},$$

wherein M represents the cylinder sinogram measurements.

17. The program according to claim 16, wherein the simple update iterative algorithm comprises an equation $$\varepsilon_k^{(n)} = \varepsilon_k^{(n-1)} + \frac{\sum_{j \neq k} \varepsilon_j^{(n,k)} \sum_t T_{t,kj} \omega_{\rho\theta\zeta t,kj} (M_{\rho\theta\zeta t} - \overline{M}_{\rho\theta\zeta t}(\varepsilon_k^{(n,k)}))}{\sum_{j \neq k} \varepsilon_j^{(n,k)} \sum_{j' \neq k} \varepsilon_{j'}^{(n,k)} \sum_t T_{t,kj} T_{t,kj'} \sum_{\rho,\theta,\zeta} \omega_{\rho\theta\zeta t,kj} \omega_{\rho\theta\zeta t,kj'}},$$

wherein $$\varepsilon^{(n,k)} = \{\varepsilon_0^{(n)}, \varepsilon_1^{(n)}, \ldots, \varepsilon_{k-1}^{(n)}, \varepsilon_k^{(n-1)}, \varepsilon_{k+1}^{(n-1)}, \ldots\},$$

and n is an iteration number.

18. The program according to claim 16, wherein the simple update iterative algorithm comprises an equation $$\varepsilon_k^{(n)} = \varepsilon_k^{(n-1)} + \frac{\sum_{j \neq k} \varepsilon_j^{(n-1)} \sum_t \omega_{\rho\theta\zeta t,kj} T_{t,kj} (M_{\rho\theta\zeta t} - \overline{M}_{\rho\theta\zeta t}(\varepsilon^{(n-1)}))}{\sum_{j \neq k} \varepsilon_j^{(n-1)} \sum_t \omega_{\rho\theta\zeta t,kj} T_{t,kj} E_{\rho\theta\zeta t}^{(n-1)}},$$

wherein $$E_{\rho\theta\zeta t}^{(n-1)} = \frac{1}{2} \sum_{ij} \omega_{\rho\theta\zeta t,ij} T_{t,ij} (\varepsilon_i^{(n-1)} + \varepsilon_j^{(n-1)}),$$

and n is an iteration number.

19. The program according to claim 17 wherein an initial condition of the simple update iterative algorithm comprises a value represented by an equation $$\varepsilon_k^{(0)} = \sqrt{\frac{\frac{1}{2}\sum_{j \neq k}\sum_t \omega_{\rho\theta\zeta t,kj} T_{t,kj} |M_{\rho\theta\zeta t}|}{\frac{1}{2}\sum_{j \neq k}\sum_t \omega_{\rho\theta\zeta t,kj} T_{t,kj} \frac{1}{2}\sum_{lm} \omega_{\rho\theta\zeta t,lm} T_{t,lm}}}.$$

20. The program according to claim 18 wherein an initial condition of the simple update iterative algorithm comprises a value represented by an equation $$\varepsilon_k^{(0)} = \sqrt{\frac{\frac{1}{2}\sum_{j \neq k}\sum_t \omega_{\rho\theta\zeta t,kj} T_{t,kj} |M_{\rho\theta\zeta t}|}{\frac{1}{2}\sum_{j \neq k}\sum_t \omega_{\rho\theta\zeta t,kj} T_{t,kj} \frac{1}{2}\sum_{lm} \omega_{\rho\theta\zeta t,lm} T_{t,lm}}}.$$

* * * * *